US008304405B2

(12) United States Patent
Lulla et al.

(10) Patent No.: US 8,304,405 B2
(45) Date of Patent: *Nov. 6, 2012

(54) COMBINATION OF AZELASTINE AND CICLESONIDE FOR NASAL ADMINISTRATION

(75) Inventors: Amar Lulla, Mumbai (IN); Geena Malhotra, Mumbai (IN)

(73) Assignee: Cipla Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 12/508,393

(22) Filed: Jul. 23, 2009

(65) Prior Publication Data

US 2009/0318397 A1   Dec. 24, 2009

Related U.S. Application Data

(62) Division of application No. 10/518,016, filed as application No. PCT/GB03/02557 on Jun. 13, 2003, now Pat. No. 8,168,620.

(30) Foreign Application Priority Data

Jun. 14, 2002   (GB) ................... 0213739.6

(51) Int. Cl.
*A01N 45/00* (2006.01)
(52) U.S. Cl. ...................................... 514/171
(58) Field of Classification Search .................. None
See application file for complete search history.

(56) References Cited

U.S. PATENT DOCUMENTS

| | | | |
|---|---|---|---|
| 2,837,464 A | 6/1958 | Nobile | |
| 3,067,197 A | 12/1962 | Agnello et al. | |
| 3,312,590 A | 4/1967 | Elks et al. | |
| 3,506,694 A | 4/1970 | Oxley | |
| 3,557,162 A | 1/1971 | Voorschoten et al. | |
| 3,639,434 A | 2/1972 | Oxley et al. | |
| 3,755,302 A | 8/1973 | Ercoli et al. | |
| 3,828,080 A | 8/1974 | May et al. | |
| 3,856,828 A | 12/1974 | Phillipps et al. | |
| 3,891,631 A | 6/1975 | Phillipps et al. | |
| 3,981,894 A | 9/1976 | Phillipps et al. | |
| 3,989,686 A | 11/1976 | Phillipps et al. | |
| 4,093,721 A | 6/1978 | Phillipps et al. | |
| 4,113,680 A | 9/1978 | Kamano et al. | |
| 4,187,301 A | 2/1980 | Edwards | |
| 4,188,385 A | 2/1980 | Edwards | |
| 4,198,403 A | 4/1980 | Alvarez | |
| 4,221,787 A | 9/1980 | Bodor et al. | |
| 4,261,984 A | 4/1981 | Alvarez | |
| 4,263,289 A | 4/1981 | Edwards | |
| 4,267,173 A | 5/1981 | Draper | |
| 4,285,937 A | 8/1981 | Kalvoda | |
| 4,310,466 A | 1/1982 | Edwards | |
| 4,335,121 A | 6/1982 | Phillipps et al. | |
| 4,377,575 A | 3/1983 | Stache et al. | |
| 4,472,393 A | 9/1984 | Shapiro | |
| 4,607,028 A | 8/1986 | Schmidlin | |
| 4,710,495 A | 12/1987 | Bodor | |
| 4,861,765 A | 8/1989 | Mitsukuchi et al. | |
| 4,992,474 A | 2/1991 | Skidmore et al. | |
| 4,994,439 A | 2/1991 | Longnecker et al. | |
| 4,996,335 A | 2/1991 | Bodor | |
| 5,063,222 A | 11/1991 | Komoto et al. | |
| 5,081,113 A | 1/1992 | Claussner et al. | |
| 5,086,050 A | 2/1992 | Hettche et al. | |
| 5,164,194 A | 11/1992 | Hettche | |
| 5,202,316 A | 4/1993 | Claussner et al. | |
| 5,232,919 A | 8/1993 | Scheffler et al. | |
| 5,271,946 A | 12/1993 | Hettche | |
| 5,362,721 A | 11/1994 | Stache et al. | |
| 5,420,120 A | 5/1995 | Boltralik | |
| 5,608,093 A | 3/1997 | Stache et al. | |
| 5,658,549 A | 8/1997 | Akehurst et al. | |
| 5,658,919 A | 8/1997 | Ratnaraj et al. | |
| 5,707,984 A | 1/1998 | Tjoeng et al. | |
| 5,837,699 A | 11/1998 | Sequeira et al. | |
| 5,849,265 A | 12/1998 | Li-Bovet et al. | |
| 5,889,015 A | 3/1999 | Sequeira et al. | |
| 5,914,122 A | 6/1999 | Otterbeck et al. | |
| 5,972,920 A | 10/1999 | Seidel | |
| 5,981,517 A | 11/1999 | Bodor | |
| 6,017,963 A | 1/2000 | Alfonso et al. | |
| 6,057,307 A | 5/2000 | Sequeira et al. | |
| 6,127,353 A | 10/2000 | Yuen et al. | |
| 6,136,294 A | 10/2000 | Adjei et al. | |
| 6,197,761 B1 | 3/2001 | Biggadike et al. | |

(Continued)

FOREIGN PATENT DOCUMENTS

AU   2003244799 B2   12/2003

(Continued)

OTHER PUBLICATIONS

Schmidt et al., The new topical steroid ciclesonide is effective in the treatment of allergic rhinitis, Journal of Clinical Pharmacology, vol. 39, No. 10, pp. 1062-1069, 1999.*
Applicants response to foreign communication—EP 03738280.1, May 22, 2006, 36 pages.
Applicants response to foreign communication—EP 03738280.1, Jan. 18, 2008, 14 pages.
Busse, W. W., et al., "Corticosteroid-sparing effect of azelastine in the management of bronchial asthma," American Journal of Respiratory and Critical Care Medicine, 1996, pp. 122-127, vol. 153, No. 1, American Lung Association, New York, NY, XP-000604179.
Foreign communication from the priority application—Search Report, GB 0213739.6, Nov. 22, 2002, 4 pages.
Foreign communication from the priority application—International Search Report, PCT/GB03/02557, Sep. 17, 2003, 3 pages.

(Continued)

*Primary Examiner* — James H. Alstrum-Acevedo
*Assistant Examiner* — Thor Nielsen
(74) *Attorney, Agent, or Firm* — Conley Rose, P.C.; Rodney B. Carroll

(57) ABSTRACT

A pharmaceutical product or formulation, which comprises azelastine or a pharmaceutically acceptable salt, solvate or physiologically functional derivative thereof, and a steroid, or a pharmaceutical acceptable salt, solvate or physiologically functional derivative thereof, preferably the product or formulation being in a form suitable for nasal or ocular administration.

16 Claims, No Drawings

U.S. PATENT DOCUMENTS

| | | |
|---|---|---|
| 6,261,539 B1 | 7/2001 | Adjei et al. |
| 6,294,153 B1 | 9/2001 | Modi |
| 6,319,513 B1 | 11/2001 | Dobrozsi |
| 6,330,938 B1 | 12/2001 | Herve et al. |
| 6,391,340 B1 | 5/2002 | Malmqvist-Granlund et al. |
| 6,395,300 B1 | 5/2002 | Straub et al. |
| 6,416,743 B1 | 7/2002 | Fassberg et al. |
| 6,525,228 B2 | 2/2003 | Chauvin et al. |
| 6,537,983 B1 | 3/2003 | Biggadike et al. |
| 6,583,180 B2 | 6/2003 | Link et al. |
| 6,787,532 B2 | 9/2004 | Biggadike et al. |
| 6,921,757 B2 | 7/2005 | Cuenoud et al. |
| 7,101,866 B2 | 9/2006 | Biggadike et al. |
| 7,244,742 B2 | 7/2007 | Pieper et al. |
| 7,776,315 B2 | 8/2010 | Pairet et al. |
| 2002/0061281 A1 | 5/2002 | Osbakken et al. |
| 2002/0076382 A1 | 6/2002 | Kaplan et al. |
| 2002/0081266 A1 | 6/2002 | Woolfe et al. |
| 2002/0103392 A1 | 8/2002 | Stache et al. |
| 2002/0165211 A1 | 11/2002 | Biggadike et al. |
| 2002/0173496 A1 | 11/2002 | Biggadike |
| 2002/0177581 A1 | 11/2002 | Biggadike |
| 2003/0018019 A1 | 1/2003 | Meade et al. |
| 2003/0073676 A1 | 4/2003 | Biggadike et al. |
| 2003/0109511 A1 | 6/2003 | Biggadike et al. |
| 2003/0144257 A1 | 7/2003 | Biggadike et al. |
| 2003/0158163 A1 | 8/2003 | Cuenoud et al. |
| 2004/0053904 A1 | 3/2004 | Komoto et al. |
| 2004/0136918 A1* | 7/2004 | Garrett et al. ............. 424/46 |
| 2004/0204399 A1 | 10/2004 | Osbakken et al. |
| 2004/0235807 A1 | 11/2004 | Weinrich et al. |
| 2004/0242638 A1 | 12/2004 | Yanni et al. |
| 2005/0163724 A1 | 7/2005 | Miyadia et al. |
| 2005/0192261 A1 | 9/2005 | Jost-Price et al. |
| 2006/0025391 A1 | 2/2006 | Lulla et al. |
| 2006/0110331 A1 | 5/2006 | Dang et al. |
| 2006/0228306 A1 | 10/2006 | Lane |
| 2007/0020330 A1 | 1/2007 | Dang et al. |
| 2009/0286762 A1 | 11/2009 | Myles et al. |
| 2010/0152147 A1 | 6/2010 | Fuge et al. |

FOREIGN PATENT DOCUMENTS

| | | |
|---|---|---|
| BE | 889563 A | 11/1981 |
| DE | 1059906 | 6/1959 |
| DE | 2164058 A1 | 7/1972 |
| DE | 3836579 A1 | 5/1989 |
| DE | 19947234 A1 | 9/1999 |
| DE | 10152369 A1 | 5/2002 |
| EP | 0004773 | 10/1979 |
| EP | 0057401 | 8/1982 |
| EP | 0179583 | 4/1986 |
| EP | 0393658 | 10/1990 |
| EP | 0416951 | 3/1991 |
| EP | 0780127 * | 6/1997 |
| EP | 0780127 A1 | 6/1997 |
| EP | 1519731 B1 | 4/2009 |
| EP | 2072051 A1 | 6/2009 |
| GB | 1191965 | 5/1970 |
| GB | 1296458 | 11/1972 |
| GB | 1384372 | 2/1975 |
| GB | 1438940 | 6/1976 |
| GB | 1517278 | 7/1978 |
| GB | 2079755 | 1/1982 |
| GB | 2088877 | 6/1982 |
| GB | 2140800 | 12/1984 |
| GB | 2389530 A | 12/2003 |
| IL | 109656 | 2/1998 |
| JP | 04208267 | 7/1992 |
| JP | 8291072 | 11/1996 |
| JP | 8291073 | 11/1996 |
| JP | 2002-053485 | 2/2002 |
| WO | 8504589 A1 | 10/1985 |
| WO | 8903390 | 4/1989 |
| WO | 9015816 | 12/1990 |
| WO | 9104252 | 4/1991 |
| WO | 9214472 | 9/1992 |
| WO | 9531964 | 11/1995 |
| WO | 9619199 | 6/1996 |
| WO | 9632151 | 10/1996 |
| WO | 9701337 A1 | 1/1997 |
| WO | 9705136 | 2/1997 |
| WO | 9715298 | 5/1997 |
| WO | 9721721 | 6/1997 |
| WO | 9721724 | 6/1997 |
| WO | 9724365 | 7/1997 |
| WO | 9740836 | 11/1997 |
| WO | 9746243 A1 | 12/1997 |
| WO | 9817676 | 4/1998 |
| WO | 9834596 | 8/1998 |
| WO | 9848839 A1 | 11/1998 |
| WO | 9901467 | 1/1999 |
| WO | 9925359 | 5/1999 |
| WO | 9932089 | 7/1999 |
| WO | 0016814 | 3/2000 |
| WO | 0033892 | 6/2000 |
| WO | 0038811 | 7/2000 |
| WO | 0048587 | 8/2000 |
| WO | 0049993 | 8/2000 |
| WO | 0066522 | 11/2000 |
| WO | 0104118 | 1/2001 |
| WO | 0120331 | 3/2001 |
| WO | 0154481 | 8/2001 |
| WO | 0154664 | 8/2001 |
| WO | 0157025 | 8/2001 |
| WO | 0162722 | 8/2001 |
| WO | 0178736 | 10/2001 |
| WO | 0178739 | 10/2001 |
| WO | 0178741 | 10/2001 |
| WO | 0178745 | 10/2001 |
| WO | 0200199 | 1/2002 |
| WO | 0200679 | 1/2002 |
| WO | 0202565 | 1/2002 |
| WO | 0207767 | 1/2002 |
| WO | 0208243 | 1/2002 |
| WO | 0211711 A2 | 2/2002 |
| WO | 0212265 | 2/2002 |
| WO | 0212266 | 2/2002 |
| WO | 0213868 | 2/2002 |
| WO | 0226723 | 4/2002 |
| WO | 0236106 | 5/2002 |
| WO | 02051422 | 7/2002 |
| WO | 02053186 | 7/2002 |
| WO | 02066422 | 8/2002 |
| WO | 02070490 | 9/2002 |
| WO | 02076933 | 10/2002 |
| WO | 02085296 | 10/2002 |
| WO | 02088167 | 11/2002 |
| WO | 02100879 | 12/2002 |
| WO | 03000241 | 1/2003 |
| WO | 03013427 | 2/2003 |
| WO | 03033000 | 4/2003 |
| WO | 03035668 | 5/2003 |
| WO | 03040691 | 5/2003 |
| WO | 03042229 | 5/2003 |
| WO | 03042230 | 5/2003 |
| WO | 03048181 | 6/2003 |
| WO | 03062259 | 7/2003 |
| WO | 03064445 | 8/2003 |
| WO | 03066033 | 8/2003 |
| WO | 03066036 | 8/2003 |
| WO | 03066656 | 8/2003 |
| WO | 03072592 | 9/2003 |
| WO | 03086399 | 10/2003 |
| WO | 03105856 A1 | 12/2003 |
| WO | 2004013156 | 2/2004 |
| WO | 2004019955 A1 | 3/2004 |
| WO | 2008012338 A2 | 1/2008 |
| ZA | 872389 | 4/1987 |

OTHER PUBLICATIONS

Foreign communication from the priority application—International Preliminary Examination Report, PCT/GB03/02557, Aug. 26, 2004, 6 pages.

Foreign communication from a related counterpart application—Examination Report, EP Application 03738280.1, Nov. 10, 2005, 4 pages.

Foreign communication from a related counterpart application—Examination Report, EP Application 03738280.1, Jul. 18, 2007, 5 pages.

May, Percy, et al., "May's Chemistry of Synthetic Drugs," Fifth Edition, 1964, pp. 12-17, Longmans.

Patent application entitled "Combination of azelastine and steroids," by Amar Lulla, et al., filed Jul. 23, 2009 as U.S. Appl. No. 12/508,388.

Portman, D. et al., Acceptability of local treatment of allergic rhinitis with a combination of a corticoid (beclomethasone) and an antihistaminic (azelastine), Database Medline, 2000, vol. 121, No. 4, pp. 273-279, XP-002252974.

Office Action dated Jan. 23, 2009, (27 pages), U.S. Appl. No. 10/518,016, filed Jul. 6, 2005.

ABPI Compendium of Data Sheets and Summaries of Product Characteristics, 1999-2000, Cover page, p. 43 and Index p. 1882, Datapharm Publications Limited, London, Great Britain.

Dykewicz, Mark S., et al., "Diagnosis and Management of Rhinitis: Complete Guidelines of the Joint Task Force on Practice Parameters in Allergy, Asthma and Immunology," Annals of Allergy, Asthma, & Immunology, vol. 81, Nov. (Part II) 1998, pp. 478-518.

Foreign communication from a related counterpart application—Notice of Opposition, EP Application 03738280.1, Feb. 22, 2010, 22 pages.

Office Action (Final) dated Apr. 28, 2010, (29 pages), U.S. Appl. No. 10/518,016, filed Jul. 6, 2005.

Preservative, definition of. Composite definition of preservative in the Medical dictionary, from internet site http://medical-dictionary.thefreedictionary.com/preservative, dated Nov. 4, 2009, 3 pages.

Herrero, Vanrell, R., "Preservatives in Ophthalmic Formulations: An Overview," Arch. Soc. Esp. Oftalmol, 2007, vol. 82., pp. 531-532.

Hodges, Norman, et al., "Antimicrobial Preservative Efficacy Testing," Handbook of Microbiological Quality Control, Pharmaceuticals and Medical Devices, 2000, p. 168 Plus cover page and publication page, Taylor & Francis Publisher, USA and Canada.

Johnson, Malcom, "Development of fluticasone propionate and comparison with other inhaled corticosteroids," J. Allergy Clin. Immunol., Apr. 1998, vol. 101, No. 4, Part 2, pp. S434-S439.

Patent Application entitled "Combination of Azelastine and Steriods," by Amar Lulla, et al., filed Sep. 10, 2010 as U.S. Appl. No. 12/879,515.

Office Action dated Sep. 30, 2010, U.S. Appl. No. 12/508,388, filed Jul. 23, 2009, 22 pages.

Product Information, Nasonex®, Aug. 2001, 22 pages, Schering Corporation, Kenilworth, NJ, US.

Product Specification Bulletin, Avicel® RC-591, Bulletin AVC591-SPEC-02/09.RS, 2 pages, FMC BioPolymer.

Product Specification Bulletin, Avicel® CL-611, Bulletin AVC611-SPEC-02/09.RS, 2 pages, FMC BioPolymer.

Ratner, Paul H., et al., "Combination therapy with azelastine hydrochloride nasal spray and fluticasone propionate nasal spray in the treatment of patients with seasonal allergic rhinitis," Annals of Allergy, Asthma & Immunology, Jan. 2008, vol. 100, Cover page, publishing page, pp. 74-81.

Ratner, Paul H., et al., "A Comparison of the Efficacy of Fluticasone Propionate Aqueous Nasal Spray and Loratadine, Alone and in Combination, for the Treatment of Seasonal Allergic Rhinitis," The Journal of Family Practice, Aug. 1998, vol. 47, No. 2, pp. 118-125, Appleton & Lange.

Reddy, Indra K., ed., "Ocular Therapeutics and Drug Delivery: A Multi-Disciplinary Approach," 1996, pp. 382-385 plus cover page and publication page, Technomic Publishing Company, Inc.

Safety Data Sheet, SDS No. 110556, Jul. 4, 2008, V14, Flonase Nasal Spray, 5 pages, GlaxoSmithKline.

Safety Data Sheet, SDS No. 110536, Jun. 23, 2008, V13, Beconase Hayfever Allergy Spray, 5 pages, GlaxoSmithKline.

Salib Rami Jean, et al., "Safety and Tolerability Profiles of Intranasal Antihistamines and Intranasal Corticosteroids in the Treatment of Allergic Rhinitis," Drug Safety 2003, vol. 26, No. 12, Cover page, publication page, pp. 863-893, ADIS Data Information BV.

Simpson, Richard J., "Budesonide and terfenadine, separately and in combination, in the treatment of hay fever," Annals of Allergy, Dec. 1994, vol. 73, Cover page, publication page, pp. 497-502.

Spector, Sheldon, "Ideal pharmacotherapy for allergic rhinitis," J Allergy Clin Immunol, 1999, vol. 103, No. 3, Part 2, pp. S386-S387, Mosby, Inc.

Wang, De-Yun, "Treatment of Allergic Rhinitis: H1-Antihistamines and Intranasal Steroids," Current Drug Targets—Inflammation & Allergy, 2002, vol. I, pp. 215-220, Bentham Science Publishers Ltd.

Wiseman, Lynda R., et al., "Intranasal Fluticasone Propionate: A Reappraisal of its Pharmacology and Clinical Efficacy in the Treatment of Rhinitis," Drugs, 1997, vol. 53, No. 5, pp. 885-907, Adis International Limited.

World Review 2001: The Pharmaceutical Market, vol. 1 International, IMS Health, 2001, cover, preface, and copyright pages plus pp. 4-42 and 5-1 through 5-11, IMS A.G.

Applicant Response to foreign communication EP Patent 1519731, Aug. 11, 2011, 252 pages.

ABPI Data Sheet Compendium, 1995-96, cover page plus pp. 38-39, Datapharm Publications Limited, London, Great Britain.

Akerlund, Anders, et al., "Clinical trial design, nasal allergen challenge models, and considerations of relevance to pediatrics, nasal polyposis, and different classes of medication," J. Allergy Clin. Immunol., Mar. 2005, vol. 115, No. 3, pp. S460-S482.

Applicants response to foreign communication—KR10-2004-7020819, Dec. 27, 2010, 18 pages.

Applicants response to foreign communication—EP 03738280.1 (EP Patent 1519731), Sep. 6, 2010, 15 pages.

Applicants response to foreign communication—CA 2489427, Dec. 20, 2010, 10 pages.

Avicel® RC/CL, Microcrystalline Cellulose and Carboxymethylcellulose Sodium, NF Dispersible Cellulose, BP, Specifications and Analytical Methods, RC-16 Updated Oct. 1995 (Feb. 1999), 6 pages, FMC BioPolymer.

Opposition to EP 1518731, Aug. 8, 2011, 19 pages.

Aurora, Jack, "Nasal Delivery; Development of Nasal Delivery Systems: A Review," Drug Delivery Technology, vol. 2, No. 7, Oct. 2002, 8 pages, http://www.drugdeliverytech.com/ME2/Segments/Publications:Article&id=9EB19EB2F29F462089CE081473F5F3CA.

Baena-Cagnani, Carlos E., "Safety and Tolerability of Treatments for Allergic Rhinitis in Children," Drug Safety 2004, vol. 27, No. 12, pp. 883-898, ADIS Data Information BV.

Barnes, M. L., et al., "Effects of levocetirizine as add-on therapy to fluticasone in seasonal allergic rhinitis," Clinical and Experimental Allergy, Jan. 27, 2006, vol. 36, pp. 676-684, Blackwell Publishing Ltd.

Berge, Stephen M., et al., "Pharmaceutical Salts," Journal of Pharmaceutical Sciences, vol. 66, No. 1, Jan. 1977, pp. 1-19.

Block, John H., et al., "Inorganic Medicinal and Pharmaceutical Chemistry," 1986, cover, publication, and preface pages plus p. 100, Indian Edition, Varghese Publishing House, Bombay, India.

Cipla Sixty-Ninth Annual Report 2004-2005, cover pages, information page, plus pp. 3, 5, and 44.

Di Lorenzo, G., et al., "Randomized Placebo-controlled Trial Comparing fluticasone aqueous nasal spray in mono-therapy, fluticasone plus cetirizine, fluticasone plus montelukast and cetirizine plus montelukast for seasonal allergic rhinitis," Clin. Exp. Allergy, 2004, vol. 34, pp. 259-267., Blackwell Publishing Ltd.

Duonase Data Sheet, "The Complete Rhinitis Control," 6 pages, Cipla Limited, Mumbai, India, 1900.

Drouin, Michel A., et al., "Adding Loratadine to Topical Nasal Steroid Therapy Improves Moderately Severe Seasonal Allergic Rhinoconjunctivitis," Advances in Therapy, vol. 12, No. 6, Nov./Dec. 1995, pp. 340-349, Health Communications Inc.

File history of Australian Patent Application No. AU2003244799, 38 pages, 1900.

File history of Brazilian Patent Application No. PI 0312128-3, 27 pages, 1900.

File history of Canadian Patent Application No. 2,489,427, 19 pages, 1900.

File history of Korean Patent Application No. 10-2004-7020819, 89 pages.

File history of Mexican Patent Application No. PA/a/2004/01266 (now Patent No. 265349), 86 pages.

File history of Polish Patent Application No. P-373001, 95 pages, 1900.
File history of Russian Patent Application No. RU 2361593 C2, 65 pages, 1900.
File history of South African Patent Application No. 2005/0331 (now Patent No. 2005/0331), 18 pages.
Foreign communication from a related counterpart application—CA2,489,427, Examination Report, Jun. 18, 2010, 3 pages.
Foreign communication from a related counterpart application—CA2,489,427, Examination Report, Mar. 24, 2011, 2 pages.
Foreign communication from a related counterpart application—EP Application 03738280.1, Examination Report, Nov. 10, 2005, 4 pages.
Foreign communication from a related counterpart application—EP Application 03738280.1, Examination Report, Jul. 18, 2007, 5 pages.
Foreign communication from a related counterpart application—EP Application 03738280.1, Notice of Intent to Grant, Oct. 23, 2008, 6 pages.
Foreign communication from a related counterpart application—Summons to Attend Oral Proceedings, EP Application 03738280.1, Feb. 8, 2011, 1 page.
Foreign communication from a related counterpart application—AU2003244799, Examination Report, Nov. 20, 2007, 2 pages.
Foreign communication from a related counterpart application—KR 10-2004-7020819, Examination Report, Aug. 26, 2010, 8 pages.
Foreign communication from a related counterpart application—Examination Report, RU 2005100781, Apr. 23, 2007, 6 pages.
Foreign communication from a related counterpart application—Examination Report, RU 2005100781, May 23, 2008, 3 pages.
Foreign communication from a related counterpart application—Translation of Office Action, Israel Patent Application 165771, Jul. 11, 2011, 3 pages.
Galant, Stanley P., et al., "Clinical Prescribing of Allergic Rhinitis Medication in the Preschool and Young School-Age Child, What are the Options?," BioDrugs2001, vol. 15, No. 7, pp. 453-463, ADIS International Ltd.
Gennaro, Alfonso R., ed., et al., Remington: The Science and Practice of Pharmacy, 2000, 20th edition, vol. 1, pp. 785, 830, 831 plus cover page and publication page, Lippincott Williams & Wilkins.
Gilbert, Peter, et al., "Preservation of Pharmaceutical Products," Encyclopedia of Pharmaceutical Technology, 2002, 2nd edition, vol. 3, p. 2278 plus cover page and publication page, Marcel Dekker, Inc.
Hodges, N. A., et al., "Preservative Efficacy Tests in Formulated Nasal Products: Reproducibility and Factors Affecting Preservative Activity," J. Pharm. Pharmacol., 1996, vol. 48, pp. 1237-1242.
Howarth, P. H., "A comparison of the anti-inflammatory properties of intranasal corticosteroids and antihistamines in allergic rhinitis," Allergy 2000, vol. 62, pp. 6-11, Munksgaard 2000.
Juniper, E F., et al., "Comparison of beclomethasone dipropionate aqueous nasal spray, astemizone, and the combination in the prophylactic treatment of ragweed pollen-induced rhinoconjunctivitis," Journal of Allergy and Clinical Immunology, Mar. 1989, vol. 83, No. 3, Cover page, Publications page, pp. 627-633, American Academy of Allergy and Immunology, C.V. Mosby Co.
McNeely, Wendy, et al., "Intranasal Azelastine: A Review of its Efficacy in the Management of Allergic Rhinitis," Drugs, 1998, vol. 56, No. 1, pp. 91-114.
Meltzer, Eli O., "Allergic rhinitis: Managing the pediatric spectrum," Allergy and Asthma Proceedings, Jan.-Feb. 2006, vol. 27, No. 1, pp. 2-8, Oceanside Publications, Inc., USA.
Nielsen, Lars P., "Comparison of Intranasal Corticosteroids and Antihistamines in Allergic Rhinitis, A Review of Randomized, Controlled Trials," Am. J. Respir Med. 2003, vol. 2, No. 1, Cover page, publishing page, pp. 55-65., ADIS International Limited.
Nielsen, Lars Peter, et al., "Intranasal Corticosteroids for Allergic Rhinitis, Superior Relief?," Drugs 2001, vol. 61, No. 11, pp. 1563-1579, ADIS International Ltd.
Office Action dated Feb. 16, 2011, (22 pages), U.S. Appl. No. 10/518,016, filed Jul. 6, 2005.
Office Action (Final) dated Feb. 18, 2011 (23 pages), U.S. Appl. No. 12/508,388, filed Jul. 23, 2009.
Pre-Grant Opposition, Indian Patent Application 2092/KOLNP/2007 dated Jun. 8, 2007, 183 pages.

Prescribing Information for Astepro®, Nov. 2010, 20 pages, Meda Pharmaceuticals Inc., Somerset, NJ, US.
Prescribing Information for Rhinocort Aqua™, Dec. 2010, 32 pages, AstraZeneca LP, Wilmington, DE, US.
"Azelastine," STN Registry No. 58581-89-8, STN Registry File, Retrieved Nov. 23, 2010, p. 1.
"Fluticasone Furoate," STN Registry No. 397864-44-7, STN Registry File, Retrieved Nov. 23, 2010, p. 1.
Astelin (azelastine hydrochloride) Nasal Spray, MedPointe Pharmaceuticals, 2006, U.S Physicians Desk Reference, pp. 1876-1877.
Veramyst (fluticasone furoate) Nasal Spray, GlaxoSmithKline, 2007, Summary Sheet, pp. 1-20.
Astepro (azelastine HCI) Nasal Spray 0.15%, Meda Pharmaceuticals Inc., 2009, Press Release, pp. 1-4.
Aigbirhio, Franklin I., et al., "Automated radiosynthesis of no-carrier-added [S-fluoromethyl-18F]Fluticasone propionate as a radiotracer for lung deposition studies with PET," Journal of Labelled Compounds and Radiopharmaceuticals, vol. 39, No. 7, 1997, pp. 569-584.
Austin, et al., "Mometasone furoate is a less specific glucocorticoid than fluticasone propionate," Eur. Respir. J., 2002, vol. 20, pp. 1386-1392.
Banov, et al., "Once daily intranasal fluticasone propionate is effective for perennial allergic rhinitis," Annals of Allergy, 1994, vol. 73, pp. 240-246.
Barnes, Peter J., "Chronic obstructive pulmonary disease: new opportunities for drug development," Trends in Pharmacological Sciences, vol. 19, No. 10, 1998, pp. 415-423.
Barnes, Peter J., "Novel approaches and targets for treatment of chronic obstructive pulmonary disease," American Journal of Respiratory and Critical Care Medicine, vol. 160, 1999, pp. S72-S79.
Barnes, Peter J., "Efficacy of inhaled corticosteroids in asthma," The Journal of Allergy and Clinical Immunology, vol. 102, No. 4, 1998, pp. 531-538, 1998.
Baumgarten, C., et al., "Initial treatment of symptomatic mild to moderate bronchial asthma with the salmeterol/fluticasone propionate (50/250μg) combination product (SAS 40023)," European Journal of Medical Research, 2002, vol. 7, pp. 1-7.
Berstein, et al., "Treatment with intranasal fluticasone propionate significantly improves ocular symptons in patients with seasonal allergic rhinitis," Clin. Exp. Allergy, 2004, vol. 34, pp. 952-957.
Bowler, Simon, "Long acting beta agonists," Australian Family Physician, vol. 27, No. 12, 1998, pp. 1115, 1117-1118, plus cover.
Brooks, et al., "Spectrum of seasonal allergic rhinitis symptom relief with topical corticoid and oral antihistamine given singly or in combination," American Journal of Rhinology, 1996, vol. 10, No. 3, pp. 193-199.
Bryson, et al., "Intranasal fluticasone propionate: a review of its pharmacodynamic and pharmacokinetic properties, and therapeutic potential in allergic rhinitis," Drugs, 1992, vol. 43, No. 5, pp. 760-775.
Busse, William, et al., "Steroid-sparing effects of fluticasone propionate 100μg and salmeterol 50 μg administered twice daily in a single product in patients previously controlled with fluticasone propionate 250 μg administered twice daily," J. Allergy Clin. Immunol., vol. 111, No. 1, Jan. 2003, pp. 57-65.
CAS Registry No. 102113-40-6, 2004.
CAS Registry No. 90566-53-3, "Fluticasone," Nov. 16, 1984.
Chapman, et al., "Anti-inflammatory activity of inhaled mometasone furoate in allergic mice," Arzneimettelforschung ("Drug Research"), 1998, vol. 48, No. 4, pp. 384-391.
Daley-Yates, et al., "Systemic bioavailability of fluticasone propionate administered as nasal drops and aqueous nasal spray formulations," Br. J. Clin. Pharmocol., 2001, vol. 51, pp. 103-105.
Derby, et al., "Risk of cataract among users of intranasal corticosteroids," J. Allergy Clin. Immunol., 2000, vol. 105, No. 5, pp. 912-916.
Dewester, et al., "The efficacy of intranasal fluticasone propionate in relief of ocular symptoms associated with seasonal rhinitis," Allergy and Asthma Proc., 2003, vol. 24, No. 5, pp. 331-337.
Dictionary of Organic Compounds, 6th Ed., vol. 1, p. 3234 plus cover and publishing pages, definition of "fluticasone," Chapman & Hall, 1996.

Dolovich, et al., "Multicenter trial of fluticasone propionate aqueous nasal spray in ragweed allergic rhinitis," Annals of Allergy, 1994, vol. 73, No. 2, pp. 147-153.

Fowler, Stephen J., et al., "Step-down therapy with low-dose fluticasone-salmeterol combination or medium-dose hydrofluoroalkane 134a-beclomethasone alone," J. Allergy Clin. Immunol., vol. 109, No. 6, Jun. 2002, pp. 929-935.

Garner, R. C., et al., "A validation study comparing accelerator MS and liquid scintillation counting for analysis of 14C-labelled drugs in plasma, urine and faecal extracts," Journal of Pharmaceutical and Biomedical Analysis, vol. 24, 2000, pp. 197-209.

Gawchik, et al., "Comparison of intranasal triamcinolone acetonide with oral loratadine in the treatment of seasonal ragweed-induced allergic rhinitis," Am. J. Man. Care, 1997, vol. 3, No. 7, pp. 1052-1058.

Harding, "The human pharmacology of fluticasone propionate," Respiratory Medicine, 1990, vol. 84, Suppl. A, pp. 25-29.

Howland, "Fluticasone propionate: topical or systemic effects?" Clinical and Experimental Allergy, 1996, vol. 26, Suppl. 3, pp. 18-22.

Isogai, et al., "Binding affinities of mometasone furoate and related compounds including its metabolites for the glucocorticoid receptor of rat skin tissue," J. Steroid Biochem. Mol. Biol., 1993, vol. 44, pp. 141-145.

Johansson, Gunnar, et al., "Comparison of salmeterol/fluticasone propionate combination with budesonide in patients with mild-to-moderate asthma," Clin. Drug Invest., vol. 21, No. 9, 2001, pp. 633-642, 11 pages, Adis International Limited.

Juniper, Elizabeth F., et al., "Impact of inhaled salmeterol/fluticasone propionate combination product versus budesonide on the health-related quality of life of patients with asthma," Am. J. Respir. Med., vol. 1, No. 6, 2002, pp. 435-440.

Kenley, Richard A., et al., "An automated, column-switching HPLC method for analyzing active and excipient materials in both cream and ointment formulations," Drug Development and Industrial Pharmacy, vol. 11 (9 & 10), 1985, pp. 1781-1796.

Kertesz, Denis J., et al., "Thiol esters from steroid 17β-carboxylic acids: carboxylate activation and internal participation by 17 α-acylates," J. Org. Chem., vol. 51, 1986, 14 pages.

Knobil, K., et al., "Adding salmeterol is more effective than increasing the dose of fluticasone for patients with asthma who are symptomatic on low dose fluticasone," European Respiratory Review, Copenhagen, DK, vol. 12, Suppl. 29, Dec. 1998, pp. 19S-20S plus cover page.

Kooreman, et al., "The synthesis of 17-esters of corticosteroids protection of 11β-hydroxyl of the trimethylsilyl group," Synthetic Communications, vol. 1, No. 2, pp. 81-87, 1971.

Laforce, et al., "Fluticasone propionate: an effective alternative treatment for seasonal allergic rhinitis in adults and adolescents," J. Fam. Pract., 1994, vol. 38, No. 2, pp. 145-152.

Lane, S. J., et al., "Evaluation of a new capillary electrochromatography/mass spectrometry interface using short columns and high field strengths for rapid and efficient analyses," Rapid Communications in Mass Spectrometry, vol. 10, 1996, pp. 733-736.

Lewis, Sarah A., et al., "Association of specific allergen sensitization with socioeconomic factors and allergic disease in a population of Boston women," J. Allergy Clin. Immunol., vol. 107, No. 4, Apr. 2001, pp. 615-622.

Li, et al., "Synthesis of aryl 5-(2-chlorophenyl)-2-furoates under phase transfer catalysis," Synthetic Communications, vol. 32, No. 20, pp. 3081-3086, 2002.

Linder, "Symptom scores as measurements of the severity of rhinitis," Clinical Allergy, 1988, vol. 18, pp. 29-37.

Lumry, William R., "A review of the preclinical and clinical data of newer intranasal steroids in the treatment of allergic rhinitis," Allergy Clin. Immunol., Oct. 1999, 104 (4 Pt 1), pp. S150-S158 plus one correction page.

Lutsky, et al., "A novel class of potent topical antiinflammatory agents: 17-benzoylated, 7a-halogeno substituted corticosteroids," Arzneimettelforschung ("Drug Research"), 1978, vol. 29, No. 11, pp. 1662-1667.

Lyseng-Williamson, Katherine A., et al., "Inhaled salmeterol/fluticasone propionate combination in chronic obstructive pulmonary disease," Am. J. Respir. Med., vol. 1, No. 4, 2002, pp. 273-282.

Mahoney, Janette M., et al., "Drug effects on the neovascularization response to silver nitrate cauterization of the rat cornea," Current Eye Research, vol. 4, No. 5, 1985, pp. 531-535.

Meltzer, et al., "Onset of therapeutic effect of fluticasone propionate aqueous nasal spray," Ann. Allergy Asthma Immunol., 2001, vol. 86, No. 3, pp. 286-291.

Millard, Jeffrey W., et al., "Solubilization by cosolvents establishing useful constants for the log-linear model," Int'l Journal of Pharmeceutics, vol. 245, 2002, pp. 153-166.

Mistry, Nisha, et al., "Characterisation of impurities in bulk drug batches of fluticasone propionate using directly coupled HPLC-NMR spectroscopy and HPLC-MS," Journal of Pharmaceutical and Biomedical Analysis, vol. 16, 1997, pp. 697-705.

Mistry, Nisha, et al., "Impurity profiling in bulk pharmaceutical batches using 19F NMR spectroscopy and distinction between monomeric and dimeric impurities by NMR-based diffusion measurements," Journal of Pharmaceutical and Biomedical Analysis, vol. 19, 1999, pp. 511-517.

Möllmann, H., et al., Handbook of pharmacokinetic / pharmacodynamic correlation, Chapter 14, Pharmacokinetic-Pharmacodynamic Correlations of Corticosteroids, 323-336 plus cover and publishing pages, CRC Press, 1995.

Moreno-Vargas, et al., "Synthesis and gylcosidase inhibitory activities of 5-(1',4'-dideoxy-1',4'-imino-D-erythrosyl)-2-methyl-3-furoic acid (=5-[(3S,4R)-3,4-dihydroxypyrrolidin-2-yl]-2methylfuran-3-carboxylic acid) derivatives: new leads as selective alpha-L-fucosidase and beta-galactosidase inhibitors," Helvetica Chimica Acta, vol. 86, pp. 1894-1913, 2003.

Naedele-Risha, R., et al., "Dual components of optimal asthma therapy: scientific and clinical rationale for the use of long acting beta-agonists with inhaled corticosteroids," The Journal of the American Osteopathic Association, vol. 101, No. 9, Sep. 2001, pp. 526-533.

Nathan, et al., "A once daily fluticasone proprionate aqueous nasal spray is an effective treatment for seasonal allergic rhinitis," Annals of Allergy, 1991, vol. 67, pp. 332-338.

Nelson, Harold, S., et al., Fluticasone propionate-salmeterol combination provides more effective asthma control than low-dose inhaled corticosteroid plus montelukast, J. Allergy Clin. Immunol., vol. 106, No. 6, Dec. 2000, pp. 1088-1095.

O'Conner, B. J., "Combination therapy," Pulmonary Pharmacology and Therapeutics, vol. 11, No. 5/6, 1998, pp. 397-399.

Ong, John T. H., et al., "Micellar solubilization of timobesone acetate in aqueous and aqueous propylene glycol solutions of nonionic surfactants," Pharmaceutical Research, vol. 5, No. 11, 1988, pp. 704-708.

Ong, John T. H., et al., "Intrinsic potencies of novel thiol ester corticosteroids RS-85095 and RS-21314 as compared with clobetasol 17-propionate and fluocinonide," Arch Dermatol, vol. 125, Dec. 1989, pp. 1662-1665.

Onrust, et al., "Mometasone furoate, a review of its intranasal use in allergic rhinitis," Drugs, vol. 56, No. 4, Oct. 1998, pp. 725-745, vol. 21.

Holgate, Stephen T., Difficult Asthma, 1999, cover page and publishing information.

PCT/GB01/03495, International Preliminary Examination Report, date of completion of report: Aug. 30, 2002.

Pettersson, Bertil, et al., "Re-evaluation of the classical mycoplasma lipophilum cluster (Weisburg, et al., 1989) and description of two new clusters in the hominis group based on 16S rDNA sequences," Int'l Journal of Systematic & Evolutionary Microbiology, 2001, vol. 51, pp. 633-643, IUMS, Great Britain.

Phillips, G. H., et al., "Synthesis and structure activity relationships in a series of anti-inflammatory corticosteroid analogues, halomethyl androstane-17B-carbothioates and—17B-carboselenoates," Journal of Medicinal Chemistry, 1994, vol. 37, pp. 3717-3729.

Popper, T. L., et al., "Structure-activity relationships of a series of novel topical corticosteroids," Journal of Steroid Biochemistry, 1987, vol. 27, pp. 837-843, Pergamon Journals Ltd.

Product Information Flonase (Fluticasone proprionate) Nasal Spray 50 mcg, Mar. 2004, pp. 1-13, GlaxoSmithKline.

Product Information Rhinocort Aqua® (budesonide) Nasal Spray 32 mcg, Jan. 2005, 2 pages, AstraZeneca.

Sakagami, et al., "Mucoadhexive BDP microspheres for powder inhalation-their unique pharmacokinetic-pharmacodynamic profiles," Respiratory Drug Delivery, vol. VI, pp. 193-199, 1998.

Sandham, et al., "Synthesis and biological properties of novel glucocorticoid androstene C-17 furoate esters," Bioorganic & Medicinal Chemistry, 2004, vol. 12, pp. 5213-5224, Elsevier Limited.

Scadding, et al., "Clinical and physiological effects of fluticasone propionate aqueous nasal spray in the treatment of perennial rhinitis," Rhinology, 1991, Suppl. 11, pp. 37-43.

Settipane, et al., "Triamcinolone acetonide aqueous nasal spray in patients with seasonal ragweed allergic rhinitis: a placebo-controlled, double-blind study," Clinical Therapeutics, 1995, vol. 17, No. 2, pp. 252-263.

Shapiro, et al., "17-esters and 17,21-diesters of 9-alpha, 11-beta-dichlorocorticoids. Synthesis and anti-inflammatory activity," Steroids, vol. 9, No. 2, pp. 143-156, Feb. 1967.

Shapiro, et al., "Synthesis and structure-activity studies of corticosteroid 17-heterocyclic aromatic esters. 1. 9-alpha, 11-beta dichloro series," Journal of Medicinal Chemistry, vol. 30, No. 6, pp. 1068-1073, 1987, American Chemical Society.

Shapiro, et al., "17 heteroaroyl esters of corticosteroids 2. 11 beta hydroxy series," Journal of Medicinal Chemistry, American Chemical Society, Washington, US, vol. 30, No. 9, 1987, pp. 1581-1588.

Smith, et al., "In vitro glucocorticoid receptor binding and transcriptional activation by topically active glucocorticoids," Arzneimettelforschung, 1998, 48(II)(9), pp. 956-959.

Smith, N., et al., "Comparison of the electroosmotic flow profiles and selectivity of stationary phases used in capillary electrochromatography," Journal of Chromatography A., vol. 832, 1999, pp. 41-54.

Souness, et al., "Immunosuppressive and anti-inflammatory effects of cyclic AMP phosphodiesterase (PDE) type 4 inhibitors," Immunopharmacology, 2000, vol. 47, Nos. 2/3, pp. 127-162.

Stempel, et al., "Treatment of allergic rhinitis: an evidence-based evaluation of nasal corticosteroids versus nonsedating antihistamines," Am. J. Man. Care, 1998, vol. 4, pp. 89-96.

Study No. 03DMW062—"Pharmacokinetics of GW685698X and CC118781 (fluticasone propionate) when co-administered by the intratracheal or intravenous route to the anaesthetised white pig," 2004.

Study No. B30947—"The Pharmacokinetics of GW685698X and CC118781 following intratracheal co-administration to the anaesthetised white pig," 2003.

Szefler, Stanley J., et al., Chapter 21, "Glucocorticoids in severe asthma: mechanisms of action and route of administration," Difficult Asthma, pp. 371-375 plus cover and publishing pages, Martin Dunitz Ltd., Informa Health Care, 1999.

Tanaka, et al., "Synthesis of 4H-furo[3,2-b]indole derivatives. III (1). Preparation of 4H-furo[3,2-b]indole-2-carboxylic acid derivatives," Journal Heterocyclic Chemistry, vol. 16, pp. 785-788, Jun. 1979.

Togashi, et al., 9-fluoro-11B, 17, 21-trihyrdroxy-16a-methyl-1,4-pregnadiene-3, 20-dione 21-cyclohexanecarboxylate 17-cyclopropanecarboxylate (ST126); Oyo Yakuri, 2002, vol. 63, No. 5/6, pp. 61-77.

Ueno, et al., "Synthesis and evaluation of antiinflammatory activities of a series of corticosteroid 17. Alpha-esters containing a functional group," Journal of Medicinal Chemistry, American Chemica Society, vol. 34, No. 8, Aug. 1991, pp. 2468-2473.

Undem, et al., "Neural integration and allergic disease," J. Allergy Clin. Immunol., 2000, vol. 106, No. 5, pp. S213-S220.

The United States Pharmacopoeia, 23rd Ed., US Pharmacopoeia Convention, Inc., Rockville MD, 1995, pp. 1843-1844, "Physical Tests / (941) X-Ray Diffraction."

Van As, et al., "Once daily flluticasone propionate is as effective for perennial allergic rhinitis as twice daily beclomethasone dipropionate," J. Allergy Clin. Immunol., 1993, vol. 91, No. 6, pp. 1146-1154.

Van Bavel, et al., "Ocular efficacy and clinician overall evaluation of intranasal fluticasone proprionate (FP) versus loratadine (LOR) in seasonal allergic rhinitis (SAR)," Annals of Allergy, Asthma, & Immunology, 1997, vol. 78, p. 128, Abstract P101.

Van Der Molen, et al., "Effects of the long acting beta agonist formoterol on asthma control in asthmatic patients using inhaled corticosteroids," Thorax, vol. 52, No. 6, 1997, pp. 535-539 plus publishing information.

Wenkert, et al., "Short syntheses of furan and catechol derivatives. A synthesis of hydrourushiol1,2," Journal American Chemical Society, vol. 105, pp. 2021-2029, 1983.

Westlund, et al., "Fluticasone propionate aqueous nasal spray 200 mg once daily provides relief of ocular symptoms associated with seasonal allergic rhinitis," 57th Annual Meeting of the American Academy of Allergy, Asthma and Immunology, New Orleans LA, Mar. 16-21, 2001, Abstract No. 522.

Woodford, et al., "Activity and bioavailability of a new steroid (Timobesone acetate) in cream and ointment compared with Lidex and Dermovate creams and ointments and Betnovate cream," Int'l Journal of Pharmaceutics, 1985, vol. 26, pp. 145-155.

Observations on patentability of the object of the patent application PV 2003-352 (Czech Republic), 2003.

Notice of Opposition to the grant of patent on Patent Application No. 762/2001 (140397) (Pakistan), 2010.

CIPLA Annual Report Extract; 2010; (report shows that they launched an FF+azelastine product in 2010).

Comparative data of azelastine with steroids, 2011.

Declaration of Geena Malhotra for EP1519731 dated Aug. 11, 2011.

Declaration of Joachim Maus for EP1519731 dated Aug. 10, 2011.

Vanrell, "Preservatives in ophthalmic formulations: an overview," Arch. Soc. Esp. Oftalmol., 2007, vol. 82, pp. 531-532.

Malhotra Exhibit A, Aug. 2011.

Malhotra Exhibit B, Aug. 2011.

Maus Exhibit B, Aug. 2011.

Nielsen, et al., "Intranasal corticosteroids for allergic rhinitis: superior relief?" Drugs, 2001, vol. 61, No. 11, pp. 1563-1579 plus cover and publishing pages.

Opponent's R116 Submission for EP1519731, 2011.

CIPLA's response to Statement of Opposition for EP1519731, 2011.

Shenfield, "Fixed drug combinations: which ones can be recommended?" Current Therapeutics, Dec. 1986, pp. 15-16, 22-24, and 27-29.

Opponent's Statement of Opposition for EP1519731, 2011.

Result of oral proceedings dated Oct. 12, 2011 of EP Patent No. 1519731.

Opponent's submission dated Oct. 6, 2011 to EP Patent No. 1519731.

Patentee's submission dated Oct. 5, 2011 to EP Patent No. 1519731.

Patentee's submission dated Sep. 29, 2011 regarding list of attendees at oral proceedings on EP Patent No. 1519731.

Opponent's submission dated Sep. 23, 2011 regarding list of attendees at oral proceedings on EP Patent No. 1519731.

Opponent's submission dated Sep. 23, 2011 regarding additional documents on EP Patent No. 1519731.

Patentee's submission dated Sep. 19, 2011 on EP Patent No. 1519731.

Patentee's response of Sep. 6, 2010 of EP Patent No. 1519731.

Hampel, Frank C., et al., Double-blind, placebo-controlled study of azelastine and fluticasone in a single nasal spray delivery device, Annals of Allergy, Asthma & Immunology, Aug. 2010, vol. 105, pp. 168-173.

Biggadike, Keith, Letter to the Editor, "Fluticasone furoate/fluticasone propionate—different drugs with different properties," The Clinical Respiratory Journal, 2011, pp. 183-184.

Rapid response report: summary with critical appraisal, fluticasone furoate versus fluticasone propionate for seasonal allergic rhinitis: a review of the clinical and cost-effectiveness, Jun. 13, 2011, Fluticasone Furoate for Seasonal Allergic Rhinitis.

Office Action dated Sep. 9, 2011 of U.S. Appl. No. 12/508,388, filed Jul. 23, 2009.

Search Report dated May 12, 2009 of EP 09075101.

Search Report dated May 12, 2009 of EP 09075100.

Mealy, N. E., et al., "Ciclesonide: treatment of allergic rhinitis antiallergy/antiasthmatic," Drugs of the Future, Prous Science, ES, vol. 26, No. 11, Nov. 2001, pp. 1033-1039.

Office Action dated Jul. 11, 2011 of IL Patent Application No. 165771.

Office Action dated Aug. 31, 2010 (6 pages), U.S. Appl. No. 12/374,523, filed Jan. 21, 2009.
Applicants' response dated Oct. 6, 2010 (8 pages) in U.S. Appl. No. 12/374,523, filed Jan. 21, 2009.
Office Action dated Nov. 30, 2010 (16 pages), U.S. Appl. No. 12/374,523, filed Jan. 21, 2009.
Applicants' response dated Feb. 24, 2010 2011 (8 pages) in U.S. Appl. No. 12/374,523, filed Jan. 21, 2009.
Office Action (Final) dated May 3, 2011 (8 pages), U.S. Appl. No. 12/374,523, filed Jan. 21, 2009.
Applicants' response dated Jun. 22, 2011 (9 pages) in U.S. Appl. No. 12/374,523, filed Jan. 21, 2009.
Notice of Non-responsive Amendment dated Jul. 6, 2011 (3 pages), U.S. Appl. No. 12/374,523, filed Jan. 21, 2009.
Applicants' response dated Sep. 6, 2011 (8 pages) in U.S. Appl. No. 12/374,523, filed Jan. 21, 2009.
Spector, Sheldon, "Ideal pharmacotherapy for allergic rhinitis," J Allergy Clin Immunol, vol. 103, No. 3, Part 2, pp. S386-S387, 1999.
Duonase Data Sheet, "The complete rhinitis control," 6 pages, Cipla Limited, Mumbai, India, 2004.
Product Specification Bulletin, Avicel® RC-591, Bulletin AVC591-SPEC-02/09.RS, 2 pages, FMC BioPolymer, Feb. 2009.
Product Specification Bulletin, Avicel® CL-611, Bulletin AVC611-SPEC-02109.RS, 2 pages, FMC BioPolymer, Feb. 2009.
File history of Brazilian Patent Application No. PI 0312128-3, 27 pages, Apr. 2011.
File history of Canadian Patent Application No. 2,489,427, 19 pages, Dec. 2010.
File history of Polish Patent Application No. P-373001, 95 pages, May 2011.
File history of Russian Patent Application No. RU 2361593 C2, 65 pages, Apr. 2009.
Salib, et al.; "Safety and Tolerability Profiles of Intranasal Anihistaminese and Intranasal Corticosteroids in the Treatment of Allergic Rhinitis;" Drug Safety; 2003; vol. 26, No. 12, pp. 863-893 plus cover and publishing pages.

Office Action dated Mar. 29, 2011 (3 pages) from counterpart application, AU2009243422.
Office Action dated Apr. 7, 2011 (3 pages) from counterpart application, AU2009243420.
Notice of Allowance dated Jan. 30, 2012 (66 pages), U.S. Appl. No. 10/518,016, filed Jul. 6, 2005.
Notice of Allowance dated Jan. 26, 2012, (71 pages), U.S. Appl. No. 12/879,515, filed Sep. 10, 2010.
Foreign communication from a related counterpart application—First Examination Report and Pre-Grant Opposition, Indian Patent Application No. 1696/MUMNP/2009, Jun. 27, 2012, 126 pages.
Foreign communication from a related counterpart application—First Examination Report, Indian Patent Application No. 1695/MUMNP/2009, Jun. 29, 2012, 2 pages.
Foreign communication from a related counterpart application—Final Office Action, Korean Patent Application No. 10-2011-7022532, Aug. 24, 2012, 6 pages.
Foreign communication from a related counterpart application—Final Office Action, Korean Patent Application No. 10-2011-7022533, Aug. 24, 2012, 6 pages.
Foreign communication from a related counterpart application—Examination Report, European Patent Application No. 09075100.9, Aug. 8, 2012, 6 pages.
Foreign communication from a related counterpart application—Office Action, European Patent Application No. 09075101.7, Aug. 8, 2012, 5 pages.
Nasaonex® Nasal Spray, Physicians' Desk Reference, Product Information, 2002, pp. 3131-3135, Schering Corporation.
Astelin® (azelastine hydrochloride) Nasal Spray, Physicians' Desk Reference, Product Information, 2002, pp. 3339-3341, Wallace Laboratories.

* cited by examiner

COMBINATION OF AZELASTINE AND CICLESONIDE FOR NASAL ADMINISTRATION

CROSS-REFERENCE TO RELATED APPLICATIONS

This is a Divisional Application of U.S. patent application Ser. No. 10/518,016, filed Jul. 6, 2005 and published as US 2006/0025391 A1, now U.S. Pat. No. 8,168,620 and entitled "Combination of Azelastine and Steroids," which was a filing under 35 U.S.C. 371 of International Application No. PCT/GB03/02557 filed Jun. 13, 2003, entitled "Combination of Azelastine and Steroids," claiming priority of Great Britain Patent Application No. 0213739.6 filed Jun. 14, 2002, which applications are incorporated by reference herein in their entirety.

BACKGROUND OF THE INVENTION

The present invention relates to pharmaceutical products and formulations. More particularly the present invention relates to pharmaceutical products and formulations useful for preventing or minimising allergic reactions. More particularly, but not exclusively, the present invention relates to pharmaceutical products and formulations for nasal and ocular use.

Such allergic reactions commonly comprise the allergy-related and vasomotor-related symptoms and the rhinovirus-related symptoms.

It is known to use antihistamines in nasal sprays and eye drops to treat allergy-related conditions. Thus, for example, it is known to use the antihistamine azelastine (usually as the hydrochloride salt) as a nasal spray against seasonal or perennial allergic rhinitis, or as eye drops against seasonal and perennial allergic conjunctivitis.

It is also known to treat these conditions using a corticosteroid, which will suppress nasal and ocular inflammatory conditions. Among the corticosteroids known for nasal use are, for example, beclomethasone, mometasone, fluticasone, budesonide and ciclesonide. Corticosteroids known for ocular anti-inflammatory use include betamethasone sodium, dexamethasone sodium and prednisolone acetate, for example.

It would be highly desirable, however, to provide a treatment that combines the effects of anti-histamine treatments and steroid treatments, in a pharmaceutically acceptable formulation, which is tolerated in situ, without significantly disrupting the potency of the constituent pharmaceuticals.

We have now found that, very surprisingly, azelastine (4-[(4-Chlorophenyl)methyl]-2-(hexahydro-1-methyl-1H-azepin-4-yl)-1(2H)-phthalazinone), or a pharmaceutically acceptable salt, solvate or physiologically functional derivative thereof, preferably in salt form and even more preferably in the form of the hydrochloride salt, can advantageously be combined with a steroid, or a pharmaceutically acceptable salt, solvate or physiologically functional derivative thereof, to provide a stable, very effective combination product or formulation preferably for nasal or ocular treatment. The combination can provide, in a single administration or dosing regime, the antihistaminic properties of azelastine and the anti-inflammatory (and/or other) properties of the steroid, without any significant interference between the two, or adverse reaction in situ.

SUMMARY OF THE INVENTION

In one aspect the invention provides a pharmaceutical formulation comprising azelastine or a pharmaceutically acceptable salt, solvate or physiologically functional derivative thereof and a steroid, preferably a corticosteroid, or a pharmaceutically acceptable salt, solvate or physiologically functional derivative thereof the formulation preferably being in a form suitable for administration nasally or ocularly. In an embodiment, the formulation contains the steroid in an amount from about 50 micrograms/ml to about 5 mg/ml of the formulation. In an embodiment, the formulation contains a suspension containing 0.0005% to 2% (weight/weight of the formulation) of azelastine or a pharmaceutically acceptable salt of azelastine, and from 0.5% to 1.5% (weight/weight of the formulation) of said steroid. In an embodiment, the formulation contains a suspension containing from 0.001% to 1% (weight/weight of the formulation) azelastine, or salt thereof, and from 0.5% to 1.5% (weight/weight of the formulation) steroid.

The term "physiologically functional derivative" as used herein denotes a chemical derivative of any of the specific therapeutic agents described herein having the same or similar physiological function as the free base therapeutic agent and, for example, being convertible in the body thereto. According to the present invention, examples of physiologically functional derivatives include esters.

DETAILED DESCRIPTION OF THE INVENTION

The preferred forms of formulations of the invention are nasal drops, eye drops, nasal sprays, nasal inhalation solutions or aerosols or insufflation powders.

Preferred embodiments of the invention can comprise stable aqueous solutions of azelastine or one or more of its salts, in combination with steroids which may be beclomethasone, mometasone, fluticasone, budesonide or ciclesonide, which can be used in the form of inhalation solution, pressurized aerosol, eye drops or nasal drops, and in a particular preferred embodiment, in the form of a spray (preferably a nasal spray). The spray can, for example, be formed by the use of a conventional spray-squeeze bottle or a pump vaporizer. In addition, it is also possible to use compressed gas aerosols. In a preferred embodiment, 0.03 to 3 mg of azelastine base and 0.05 to 0.15 mg of the steroid should be released per individual actuation.

The formulations preferably contain a preservative and/or stabilizer. These include, for example: ethylene diamine tetraacetic acid (edetic acid) and its alkali salts (for example dialkali salts such as disodium salt, calcium salt, calcium-sodium salt), lower alkyl p-hydroxybenzoates, chlorhexidine (for example in the form of the acetate or gluconate) and phenyl mercury borate. Other suitable preservatives are: pharmaceutically useful quaternary ammonium compounds, for example cetylpyridinium chloride, tetradecyltrimethyl ammonium bromide, generally known as "cetrimide", benzyldimethyl-[2-[2-[p-(1,1,3,3-tetramethyl-butyl)phenoxy]ethoxy]-ammonium chloride, generally known as "benzethonium chloride" and myristyl picolinium chloride. Each of these compounds may be used in a concentration of 0.002 to 0.05%, for example 0.02% (weight/volume in liquid formulations, otherwise weight/weight). Preferred preservatives among the quaternary ammonium compounds are, however, alkylbenzyl dimethyl ammonium chloride and mixtures thereof, for example the compounds generally known as "benzalkonium chloride."

The total amount of preservatives in the formulations (solutions, ointments, etc.) is preferably from 0.001 to 0.10 g, preferably 0.01 g per 100 ml of solution/suspension or 100 g of formulation.

In the case of preservatives, the following amounts of individual substances can, for example, be used: thimero sal 0.002-0.02%; benzalkonium chloride 0.002 to 0.02% (in combination with thimero sal the amount of thimero sal is, for example=0.002 to 0.005%); chlorhexidine acetate or gluconate 0.01 to 0.02%; phenyl mercuric/nitrate, borate, acetate 0.002-0.004%; p-hydroxybenzoic acid ester (for example, a mixture of the methyl ester and propyl ester in the ratio 7:3): preferably 0.05-0.15, more preferably 0.1%.

The preservative used is preferably a combination of edetic acid (for example, as the disodium salt) and benzalkonium chloride. In this combination, the edetic acid is preferably used in a concentration of 0.05 to 0.1%, benzalkonium chloride preferably being used in a concentration of 0.005 to 0.05%, more preferably 0.01%.

In the case of solutions/suspensions reference is always made to percent by weight/volume, in the case of solid or semi-solid formulations to percent by weight/weight of the formulation.

Further auxiliary substances which may, for example, be used for the formulations of the invention are: polyvinyl pyrrolidone, sorbitan fatty acid esters such as sorbitan trioleate, polyethoxylated sorbitan fatty acid esters (for example polyethoxylated sorbitan trioleate), sorbimacrogol oleate, synthetic amphotensides (tritons), ethylene oxide ethers of octylphenolformaldehyde condensation products, phosphatides such as lecithin, polyethoxylated fats, polyethoxylated oleotriglycerides and polyethoxylated fatty alcohols. In this context, polyethoxylated means that the relevant substances contain polyoxyethylene chains, the degree of polymerisation of which is generally between 2 to 40, in particular between 10 to 20. These substances are preferably used to improve the solubility of the azelastine component.

It is optionally possible to use additional isotonization agents. Isotonization agents which may, for example, be used are: saccharose, glucose, glycerine, sorbitol, 1,2-propylene glycol and NaCl.

The isotonization agents adjust the osmotic pressure of the formulations to the same osmotic pressure as nasal secretion. For this purpose, these substances are in each case to be used in such amount that, for example, in the case of a solution, a reduction in the freezing point of 0.50 to 0.56 degree C. is attained in comparison to pure water.

In Example 1, it is possible to use instead of NaCl per 100 ml of solution, for example: Glucose $1H_2O$ 3.81 g; saccharose 6.35 g; glycerine 2.2 g; 1,2-propylene glycol 1.617 g; sorbitol 3.84 g (in the case of mixtures of these substances correspondingly less may optionally be used).

Moreover, it is possible to add thickening agents to solutions according to the present invention to prevent the solution from flowing out of the nose too quickly and to give the solution a viscosity of about 1.5 to 3, preferably 2 mPa.

Such thickening agents may, for example, be: cellulose derivatives (for example cellulose ether) in which the cellulose-hydroxy groups are partially etherified with lower unsaturated aliphatic alcohols and/or lower unsaturated aliphatic oxyalcohols (for example methyl cellulose, carboxymethyl cellulose, hydroxypropylmethylcellulose), gelatin, polyvinylpyrrolidone, tragacanth, ethoxose (water soluble binding and thickening agents on the basis of ethyl cellulose), alginic acid, polyvinyl alcohol, polyacrylic acid, pectin and equivalent agents. Should these substances contain acid groups, the corresponding physiologically acceptable salts may also be used.

In the event of the use of hydroxypropyl cellulose, 0.1% by weight of the formulation, for example, is used for this purpose.

In the event of the use of Avicel RC 591 or CL 611, microcrystalline cellulose and carboxymethyl cellulose sodium commercially available from FMC BioPolymer, 0.65-3.0% by weight of the formulation, for example, is used for the purpose.

It is also possible to add to the formulations buffer substances such as citric acid/sodium hydrogensulphate borate buffer, phosphates (sodium hydrogenorthophosphate, disodium hydrogenphosphate), trometamol or equivalent conventional buffers in order, for example, to adjust the formulations to a pH value of 3 to 7, preferably 4.5 to 6.5.

The amount of citric acid is, for example, 0.01 to 0.14 g, preferably 0.04 to 0.05 g, the amount of disodium hydrogenphosphate 0.1 to 0.5 g, preferably 0.2 to 0.3 g per 100 ml of solution. The weights given relate in each case to the anhydrous substances.

In the case of solutions and suspensions, the maximum total concentration of active agent and buffer is preferably less than 5%, in particular less than 2% (weight/volume).

For the nasal application, a solution or suspension can preferably be used which is applied as an aerosol, i.e. in the form of a fine dispersion in air or in another conventional carrier gas, for example by means of a conventional pump vaporizer.

Application as a dosage aerosol is, however, also possible. Dosage aerosols are defined as being pressure packings which contain the azelastine or its salts in combination with steroid, in the form of a solution or suspension in a so-called propellant. The propellant may be a pressurized liquid chlorinated, fluorinated hydrocarbon or mixtures of various chlorinated, fluorinated hydrocarbons as well as propane, butane, isobutene or mixtures of these among themselves or with chlorinated, fluorinated hydrocarbons which are gaseous at atmospheric pressure and room temperature. Hydrofluorocarbons (HFCs), such as HFC 134a, and HFC 227a can also be used, and are preferred for environmental reasons. The pressure packing has a dosage or metering valve which, on actuation, releases a defined amount of the solution or suspension of the medicament. The subsequent very sudden vaporization of the propellant tears the solution or suspension of azelastine into the finest droplets or minute particles which can be sprayed in the nose or which are available for inspiration into the nose. Certain plastic applicators may be used to actuate the valve and to convey the sprayed suspension into the nose.

In the case of application as an aerosol, it is also possible to use a conventional adapter.

Particularly preferred embodiments of the present invention are hereinafter described and it will of course be appreciated that any of the previous description of suitable ingredients and formulation characteristics can also be applicable to the following products and formulations as provided by the present invention.

It will be appreciated, therefore, that the present invention further provides a pharmaceutical product comprising (i) azelastine, or a pharmaceutically acceptable salt, solvate or physiologically functional derivative thereof, provided in an aerosol formulation preferably together with a propellant typically suitable for MDI delivery, and (ii) at least one steroid, or a pharmaceutically acceptable salt, solvate or physiologically functional derivative thereof, provided in an aerosol formulation preferably together with a propellant typically suitable for MDI delivery, as a combined preparation for simultaneous, separate or sequential use in the treatment of conditions for which administration of one or more anti-histamine and/or one or more steroid is indicated.

The present invention also provides an aerosol formulation preferably suitable for MDI delivery comprising (i) azelastine, or a pharmaceutically acceptable salt, solvate or physiologically functional derivative thereof, and (ii) at least one steroid, or a pharmaceutically acceptable salt, solvate or physiologically functional derivative thereof, together with a propellant.

It will also be appreciated from the above, that the respective therapeutic agents of the combined preparation can be administered simultaneously, either in the same or different pharmaceutical formulations, or separately or sequentially. If there is separate or sequential administration, it will also be appreciated that the subsequently administered therapeutic agents should be administered to a patient within a time scale so as to achieve, or more particularly optimise, the above referred to advantageous synergistic therapeutic effect of a combined preparation as present in a pharmaceutical product according to the present invention.

Suitable propellants for use in pharmaceutical products of formulations as provided by the present invention include 1,1,1,2-tetrafluoroethane (HFA 134a) or 1,1,1,2,3,3,3,-heptafluoropropane (HFA 227), or a combination of both, or mono-fluoro trichloromethane and dichloro difluoromethane, in particular 1,1,1,2-tetrafluoroethane (HFA 134a) or 1,1,1,2,3,3,3-heptafluoropropane (HFA 227), with HFA 134a being preferred.

A pharmaceutical aerosol formulation according to the present invention preferably further comprises a polar cosolvent such as $C_{2-6}$ aliphatic alcohols and polyols, for example ethanol, isopropanol and propylene glycol, with ethanol often being preferred. Preferably, the concentration of the cosolvent is in the range of about 2 to 10% by weight, typically up to about 5%, of the total formulation.

A pharmaceutical aerosol formulation according to the present invention may further comprise one or more surfactants. Such surfactants can be included to stabilise the formulations and for lubrication of a valve system. Some of the most commonly used surfactants in aerosol formulations are oils derived from natural sources, such as corn oil, olive oil, cottonseed oil and sunflower seed oil, and also phospholipids. Suitable surfactants can include lecithin, oleic acid or sorbitan oleate. In an embodiment, the formulation contains from about 50 micrograms to about 1 milligram of surfactant per ml of the formulation.

A further preferred embodiment of the present invention can be where a formulation or product is provided in the form of insufflatable powder, where preferably the maximum particle size of the substance suitably does not exceed 10 μm. Azelastine or its salts and the steroid may be mixed with inert carrier substances or drawn up onto inert carrier substances. Carrier substances which may, for example, be used are: sugars such as glucose, saccharose, lactose and fructose. Also starches or starch derivatives, oligosaccharides such as dextrins, cyclodextrins and their derivatives, polyvinylpyrrolidone, alginic acid, tylose, silicic acid, cellulose, cellulose derivatives (for example cellulose ether), sugar alcohols such as mannitol or sorbitol, calcium carbonate, calcium phosphate, etc.

In one embodiment, the therapeutic agents employed have a particle size of less than about 10 μm, preferably less than 5 μm.

The use of insufflation powders can represent a preferred embodiment of the present invention and there is provided by the present invention a pharmaceutical product comprising (i) azelastine, or a pharmaceutically acceptable salt, solvate or physiologically functional derivative thereof, provided as an insufflation powder, and (ii) at least one steroid, or a pharmaceutically acceptable salt, solvate or physiologically functional derivative thereof, provided as an insufflation powder, as a combined preparation for simultaneous, separate or sequential use in the treatment of conditions for which administration of one or more anti-histamine and/or one or more steroid is indicated.

It will be appreciated from the above, that the respective therapeutic agents of the combined preparation can be administered simultaneously, either in the same or different insufflation powder formulations, or separately or sequentially. If there is separate or sequential administration as discussed above, it will also be appreciated that the subsequently administered therapeutic agents should be administered to a patient within a time scale so as to achieve, or more particularly optimise, the above referred to advantageous synergistic therapeutic effect of a combined preparation as present in a pharmaceutical product according to the present invention.

The present invention also provides an insufflation powder formulation comprising (i) azelastine, or a pharmaceutically acceptable salt, solvate or physiologically functional derivative thereof, and (ii) at least one steroid, or a pharmaceutically acceptable salt, solvate or physiologically functional derivative thereof, together with a pharmaceutically acceptable carrier or excipient therefor.

Dry insufflation powder formulations as provided by the present invention can be beneficial where it is required that therapeutic agents as employed according to the present invention are retained in the nasal cavity, and systemic side effects can be minimised or eliminated. Furthermore, insufflation powder formulations as employed in the present invention can be beneficial whereby retention of azelastine, or a pharmaceutically acceptable salt, solvate or physiologically functional derivative thereof, at the nasal mucosa is improved, and the bitter aftertaste associated with liquid anti-histamine formulations significantly reduced, whilst also exhibiting the synergistic therapeutic effect associated with the azelastine/steroid combinations provided by the present invention. By providing a dry insufflation powder formulation of azelastine, together with a steroid, having an average particle size of less than about 10 μm, the therapeutic agents can be restricted primarily to the desired target organ, the nasal mucosa.

A dry powder insufflation formulation according to the present invention can be administered by the use of an insufflator, which can produce a finely divided cloud of the dry powder. The insufflator preferably is provided with means to ensure administration of a substantially pre-determined amount of a formulation or product as provided by the present invention. The powder may be used directly with an insufflator which is provided with a bottle or container for the powder, or the powder may be filled into a capsule or cartridge, such as a gelatin capsule, or other single dose device adapted for administration. The insufflator preferably has means to open the capsule or other dose device.

Preferred combinations of therapeutic agents employed in pharmaceutical products and formulations according to the present invention (in particular nasal sprays or drops, aerosol or insufflation products and formulations as described above) comprise any one of the following combinations.

The present invention further provides, therefore, a pharmaceutical product comprising (i) azelastine, or a pharmaceutically acceptable salt thereof, and (ii) at least one steroid selected from the group consisting of beclomethasone, fluticasone, mometasone and pharmaceutically acceptable esters thereof, as a combined preparation for simultaneous, separate or sequential use in the treatment of conditions for which administration of one or more anti-histamine and/or one or more steroid is indicated. Suitably the esters can be selected from beclomethasone dipropionate, fluticasone propionate, fluticasone valerate, mometasone furoate and mometasone furoate monohydrate.

The present invention also provides a pharmaceutical formulation comprising (i) azelastine, or a pharmaceutically acceptable salt thereof, and (ii) at least one steroid selected from the group consisting of beclomethasone, fluticasone, mometasone and pharmaceutically acceptable esters thereof, together with a pharmaceutically acceptable carrier or excipient therefor. Suitably the esters can be selected from beclomethasone dipropionate, fluticasone propionate, fluticasone valerate, mometasone furoate and mometasone furoate monohydrate.

In the case of a nasal spray, a particularly preferred formulation as provided by the present invention is a nasal spray comprising azelastine, or a pharmaceutically acceptable salt thereof (preferably azelastine hydrochloride), together with mometasone either as the free base or in ester form, preferably as mometasone furoate.

Specific combinations of therapeutic agents employed in pharmaceutical products and formulations according to the present invention comprise any one of the following combinations:

azelastine hydrochloride and beclomethasone dipropionate;
azelastine hydrochloride and fluticasone propionate;
azelastine hydrochloride and fluticasone valerate;
azelastine hydrochloride and mometasone furoate; and
azelastine hydrochloride and mometasone furoate monohydrate.

There is also provided by the present invention a method for the prophylaxis or treatment in a mammal, such as a human, of conditions for which administration of one or more anti-histamine and/or one or more steroid is indicated, which method comprises administration of a therapeutically effective amount of a pharmaceutical product substantially as hereinbefore described, as a combined preparation for simultaneous, separate or sequential use in the treatment of such conditions.

The present invention also provides a method for the prophylaxis or treatment in a mammal, such as a human, of conditions for which administration of one or more anti-histamine and/or one or more steroid is indicated, which method comprises administration of a therapeutically effective amount of a pharmaceutical formulation substantially as hereinbefore described.

There is also provided by the present invention for use in the manufacture of a medicament for the prophylaxis or treatment in a mammal, such as a human, of conditions for which administration of one or more anti-histamine and/or one or more steroid is indicated, a pharmaceutical product, as a combined preparation for simultaneous, separate or sequential use in the treatment of such conditions.

There is further provided by the present invention, therefore, a process of preparing a pharmaceutical product substantially as hereinbefore described, which process comprises providing as a combined preparation for simultaneous, separate or sequential use in the treatment of conditions for which administration of one or more anti-histamine and/or one or more steroid is indicated: (i) azelastine, or a pharmaceutically acceptable salt, solvate or physiologically functional derivative thereof, and (ii) at least one steroid, or a pharmaceutically acceptable salt, solvate or physiologically functional derivative thereof.

The present invention also provides a process of preparing a pharmaceutical formulation substantially as hereinbefore described, which process comprises admixing a pharmaceutically acceptable carrier or excipient with: (i) azelastine, or a pharmaceutically acceptable salt, solvate or physiologically functional derivative thereof, and (ii) at least one steroid, or a pharmaceutically acceptable salt, solvate or physiologically functional derivative thereof. Preferably pharmaceutical formulations according to the present invention can comprise insufflation powder formulations, nasal sprays, nasal inhalation solutions or aerosols substantially as hereinbefore described.

The present invention is now illustrated by the following Examples, which do not limit the scope of the invention in any way. In Examples where only the ingredients of formulations according to the present invention are listed, these formulations are prepared by techniques well known in the art.

EXAMPLE 1

Nasal spray or nasal drops with 0.1% azelastine hydrochloride as active ingredient and steroid 0.1%

| Sr. No | Ingredients | Quantity % w/v |
|---|---|---|
| 1. | Azelastine hydrochloride | 0.1% |
| 2. | Steroid | 0.1% |
| 3. | Disodium edetate | 0.005% |
| 4. | Sodium chloride | 0.9% |
| 5. | Benzalkonium chloride | 0.001% |
| 6. | Avicel RC 591 | 1.2% |
| 7. | Citric acid monohydrate | 0.2% |
| 8. | Disodium hydrogen phosphate dodecahydrate | 0.1% |
| 9. | Purified water | |

EXAMPLE 2

Dosage aerosol giving off 0.5 mg of azelastine hydrochloride and 50 micrograms of beclomethasone dipropionate freon solvate per stroke.

About 8.0 kg of a mixture of 70 parts by weight of difluorodichloromethane and 30 parts by weight of 1,2dichlorotetrafluoroethane are cooled to about −55 degree C. in an appropriate cooling vessel. A mixture of 0.086 kg of pre-cooled sorbitantrioleate and 0.8600 kg of pre-cooled trichlorofluoromethane are dissolved with stirring into the mixture at −55 degrees C., 0.0688 kg of micronized azelastine hydrochloride, 0.00688 kg of beclomethasone dipropionate freon solvate and 0.0688 kg of micronized lactose are then incorporated in portions into the solution thereby obtained with intensive stirring. The total weight of the suspension thereby obtained is made up to 9.547 kg through addition of more of the mixture of 70 parts by weight of difluorodichloromethane and 30 parts by weight of 1,2-dichlorotetrafluoroethane cooled to about −55 degree C.

Following closure of the cooling vessel the suspension is again cooled to about −55 degrees C. under intensive stirring. It is then ready to be filled.

EXAMPLE 3

Nasal spray or nasal drops with Azelastine and steroid*

| Sr. No. | Ingredients | Quantity (% w/w) |
|---|---|---|
| | Azelastine Hydrochloride | 0.10 |
| | Fluticasone propionate | 0.0357 |
| | Glycerin | 2.60 |
| | Avicel RC 591 | 1.35 |
| | Polysorbate 80 | 0.025 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone propionate (50 mcg).

EXAMPLE 4

Nasal spray or nasal drops with Azelastine and steroid*

| Sr. No. | Ingredients | Quantity (% w/w) |
|---|---|---|
| | Azelastine Hydrochloride | 0.10 |
| | Fluticasone valerate | 0.0357 |
| | Glycerin | 2.60 |
| | Avicel RC 591 | 1.20 |
| | Polysorbate 80 | 0.030 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone valerate (50 mcg).

EXAMPLE 5

Nasal spray or nasal drops with Azelastine and steroid*

| Sr. No. | Ingredients | Quantity (% w/w) |
|---|---|---|
| | Azelastine Hydrochloride | 0.10 |
| | Fluticasone propionate | 0.0714 |
| | Glycerin | 2.60 |
| | Avicel RC 581 | 1.35 |
| | Polysorbate 80 | 0.025 |
| | Benzalkonium chloride | 0.01 |
| | Phenyl ethyl alcohol | 0.25 |
| | Purified water | q.s. |

*Each spray delivers Azelastine Hydrochloride (140 mcg) and Fluticasone propionate (50 mcg).

EXAMPLE 6

Nasal spray or nasal drops with Azelastine and steroid

| Sr. No. | Ingredients | Quantity (% w/w) |
|---|---|---|
| | Azelastine Hydrochloride | 0.10 |
| | Mometasone Furoate | 0.05173 |
| | Glycerin | 2.30 |
| | Disodium edetate | 0.005 |
| | Polysorbate 80 | 0.0125 |
| | Avicel RC 581 | 1.35 |
| | Benzalkonium chloride | 0.01 |
| | Citric acid monohydrate | 0.20 |
| | Disodium hydrogen phosphate dodecahydrate | 0.10 |
| | Purified water | q.s. |

EXAMPLE 7

Nasal spray or nasal drops with Azelastine and steroid*

| Sr. No. | Ingredients | Quantity (% w/w) |
|---|---|---|
| | Azelastine Hydrochloride | 0.10 |
| | Mometasone Furoate monohydrate | 0.05173 |
| | Glycerin | 2.60 |
| | Avicel CL 611 | 2.295 |
| | Polysorbate 80 | 0.0125 |
| | Benzalkonium chloride | 0.01 |
| | Phenyl ethyl alcohol | 0.25 |
| | Purified water | q.s. |

*Each spray delivers Azelastine Hydrochloride (140 mcg) and Mometasone furoate (50 mcg).

EXAMPLE 8

Nasal MDI with Azelastine and steroid

| Sr. No. | Ingredients | Quantity in mcg |
|---|---|---|
| | Azelastine Hydrochloride | 140 |
| | Mometasone Furoate monohydrate | 50 |
| | HFA 134a | q.s. |
| | Lecithin | 0.1% |
| | Alcohol | (up to 5%) |

EXAMPLE 9

Nasal MDI with Azelastine and steroid

| Sr. No. | Ingredients | Quantity in mcg |
|---|---|---|
| | Azelastine Hydrochloride | 140 |
| | Fluticasone propionate | 50 |
| | HFA 134a | q.s. |
| | Sorbitan trioleate | 0.1% |
| | Alcohol | (up to 5%) |

EXAMPLE 10

Nasal MDI with Azelastine and steroid

| Sr. No. | Ingredients | Quantity in mcg |
|---|---|---|
| | Azelastine Hydrochloride | 140 |
| | Fluticasone propionate | 100 |

-continued

| Sr. No. | Ingredients | Quantity in mcg |
|---|---|---|
| | HFA 134a | q.s. |
| | Oleic acid | 0.1% |

EXAMPLE 11

Nasal MDI with Azelastine and steroid

| Sr. No. | Ingredients | Quantity in mcg |
|---|---|---|
| | Azelastine Hydrochloride | 140 |
| | Fluticasone Valerate | 50 |
| | HFA 134a | q.s. |
| | Alcohol | (up to 5%) |

Insufflatable powders containing Azelastine and Steroid:

EXAMPLE 12

| Sr. No. | Ingredients | Quantity (% w/w) |
|---|---|---|
| | Azelastine Hydrochloride (Micronized) | 140 mcg |
| | Fluticasone propionate | 50 mcg |
| | Lactose | q.s. (up to 25 mcg) |

EXAMPLE 13

| Sr. No. | Ingredients | Quantity (% w/w) |
|---|---|---|
| | Azelastine Hydrochloride (Micronized) | 140 mcg |
| | Fluticasone propionate | 100 mcg |
| | Mannitol | q.s. (up to 30 mcg) |

EXAMPLE 14

| Sr. No. | Ingredients | Quantity (% w/w) |
|---|---|---|
| | Azelastine Hydrochloride (Micronized) | 140 mcg |
| | Fluticasone propionate | 250 mcg |
| | Lactose | q.s. (up to 30 mcg) |

What is claimed is:

1. A pharmaceutical formulation comprising:
azelastine, or a pharmaceutically acceptable salt thereof, and
ciclesonide, wherein said pharmaceutical formulation is in a dosage form suitable for nasal administration.

2. The pharmaceutical formulation according to claim 1, wherein said pharmaceutically acceptable salt of azelastine is azelastine hydrochloride.

3. The pharmaceutical formulation according to claim 1, wherein the formulation has a particle size of less than 10 μm.

4. The pharmaceutical formulation according to claim 1, further comprising at least one additive selected from the group consisting of a buffer, a preservative, a suspending agent, a thickening agent, a surfactant, an isotonic agent, and combinations thereof.

5. The pharmaceutical formulation according to claim 4, wherein the pH of the formulation is from 3 to 7.

6. The pharmaceutical formulation according to claim 4, wherein the surfactant, when present, comprises a polysorbate, poloxamer, or combinations thereof.

7. The pharmaceutical formulation according to claim 4, wherein the isotonic agent, when present, comprises sodium chloride, saccharose, glucose, glycerine, sorbitol, 1,2-propylene glycol or combinations thereof.

8. The pharmaceutical formulation according to claim 4, wherein said preservative, when present, is selected from edetic acid and its alkali salts, lower alkyl p-hydroxybenzoates, chlorhexidine, phenyl mercury borate, benzoic acid or a salt thereof, a quaternary ammonium compound, sorbic acid or a salt thereof, or combinations thereof.

9. The pharmaceutical formulation according to claim 4, wherein the suspending agent or thickening agent, when present, comprises cellulose derivatives, gelatin, polyvinylpyrrolidone, tragacanth, alginic acid, polyvinyl alcohol, polyacrylic acid, pectin, or combinations thereof.

10. The pharmaceutical formulation according to claim 1, which is an aqueous suspension or solution.

11. The pharmaceutical formulation according to claim 10, wherein said dosage form suitable for nasal administration comprises nasal drops or a nasal spray.

12. The pharmaceutical formulation according to claim 1, wherein said dosage form suitable for nasal administration comprises nasal drops.

13. The pharmaceutical formulation according to claim 1, wherein said dosage form suitable for nasal administration comprises nasal spray.

14. A pharmaceutical product comprising (i) azelastine, or a pharmaceutically acceptable salt thereof, and (ii) ciclesonide, as a combined preparation for use in medicine as an antihistamine and anti-inflammatory agent, said (i) azelastine, or a pharmaceutically acceptable salt thereof and (ii) ciclesonide being in a dosage form suitable for nasal administration.

15. The pharmaceutical product according to claim 14, wherein said pharmaceutically acceptable salt of azelastine is azelastine hydrochloride and ciclesonide.

16. The pharmaceutical product according to claim 14, wherein said product is formulated for use as a nasal spray in the treatment of seasonal allergic rhinitis or perennial allergic rhinitis.

* * * * *